US011298096B2

(12) United States Patent
Rouet et al.

(10) Patent No.: US 11,298,096 B2
(45) Date of Patent: Apr. 12, 2022

(54) IMAGING METHOD, CONTROLLER AND IMAGING SYSTEM, FOR MONITORING A PATIENT POST EVAR

(71) Applicant: KONINKLIJKE PHILIPS N. V., Eindhoven (NL)

(72) Inventors: Laurence Rouet, Paris (FR); Antoine Collet-Billon, Paris (FR); Cecile Dufour, Paris (FR); Robert Randall Entrekin, Kirkland, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 154 days.

(21) Appl. No.: 16/630,894

(22) PCT Filed: Jul. 12, 2018

(86) PCT No.: PCT/EP2018/068889
§ 371 (c)(1),
(2) Date: Jan. 14, 2020

(87) PCT Pub. No.: WO2019/016057
PCT Pub. Date: Jan. 24, 2019

(65) Prior Publication Data
US 2020/0155102 A1 May 21, 2020

Related U.S. Application Data

(60) Provisional application No. 62/533,308, filed on Jul. 17, 2017.

(30) Foreign Application Priority Data

Jul. 27, 2017 (EP) .................................... 17183437

(51) Int. Cl.
A61B 6/00 (2006.01)
G16H 50/50 (2018.01)
(Continued)

(52) U.S. Cl.
CPC ............ A61B 6/504 (2013.01); A61B 5/4842 (2013.01); A61B 6/032 (2013.01); A61B 6/463 (2013.01);
(Continued)

(58) Field of Classification Search
CPC ......... A61B 6/504; A61B 6/032; A61B 6/463; A61B 6/5247
See application file for complete search history.

(56) References Cited

U.S. PATENT DOCUMENTS 6,905,468 B2    6/2005  McMorrow et al.
7,805,177 B2    9/2010  Chen et al.
(Continued)

OTHER PUBLICATIONS

Joh, et al., "Ultrasound fusion imaging with real-time navigation for the surveillance after endovascular aortic aneurysm repair", Annals of Surgical Treatment and Research (ASTR), Jan. 1, 2017, vol. 92, No. 6, pp. 436-439.
(Continued)

Primary Examiner — Joseph M Santos Rodriguez

(57) ABSTRACT

The invention provides a method of patient monitoring following endovascular aneurysm repair (EVAR) with a stent graft. It particularly applies to abdominal aortic aneurysm repair. A first 3D volume scan of the stent in situ is provided and a second, subsequent 3D volume scan of the stent is also provided. One or more fiducial markers are generated in a first image derived from the first scan and in a second image derived from the second scan. The fiducial markers identify recognizable features of the stent, such as the bifurcation point in the stent graft. A rigid 3D transform mapping based on the one or more fiducial markers is extracted and then a registration is applied to the first and second scans based on the 3D rigid transform between the first and second images. A size value is derived at the same location in the aneurysm from the first and second scans. The
(Continued)

same location is determined with reference to the registered first and second images of the stent. A comparison of the size value from the first and second scans is used to assess a change in size of the aneurysm between the first and second scans. This change in size allows the clinician to evaluate disease progression.

22 Claims, 6 Drawing Sheets

(51) Int. Cl.
    *G16H 30/40*     (2018.01)
    *A61B 5/00*     (2006.01)
    *A61B 6/03*     (2006.01)
    *A61B 8/00*     (2006.01)

(52) U.S. Cl.
    CPC .............. *A61B 6/5247* (2013.01); *A61B 8/54* (2013.01); *G16H 30/40* (2018.01); *G16H 50/50* (2018.01)

(56) References Cited

U.S. PATENT DOCUMENTS

| | | |
|---|---|---|
| 8,133,181 B2 | 3/2012 | Yuk et al. |
| 2006/0020204 A1 | 1/2006 | Serra et al. |
| 2015/0196250 A1 | 7/2015 | Nair |

OTHER PUBLICATIONS

Scaife, et al., "Contemporary Applications of Ultrasound in Abdominal Aortic Aneurysm Management", Frontiers in Surgery, May 27, 2016, vol. 3, Article 29, pp. 1-7.
International Search Report and Written Opinion for International Application No. PCT/EP2018/068889, filed Jul. 12, 2018, 16 pages.
Meinel, et al., "Effect of endoleaks on changes in aortoiliac volume after endovascular repair for abdominal aortic aneurysm", Clinical Hemorheology Microcirculation, Nov. 2016, 64(2), pp. 135-147 (Abstract).
European Search Report for European Application No. 17183437.7, filed Jul. 27, 2017, 2 pages.

IMAGING METHOD, CONTROLLER AND IMAGING SYSTEM, FOR MONITORING A PATIENT POST EVAR

RELATED APPLICATIONS

This application is the U.S. National Phase application under 35 U.S.C. § 371 of International Application No. PCT/EP2018/068889 (published as WO2019016057A), filed on Jul. 12, 2018, which claims priority to and the benefit of Provisional Application No. 62/533,308 (now U.S. Patent Application Publication No. 2020155102A1), filed Jul. 17, 2017 and of European Application No. 17183437.7 (published as EP3435382A1), filed Jul. 27, 2017. These applications are hereby incorporated by reference herein.

FIELD OF THE INVENTION

This invention relates to an imaging method and apparatus for monitoring a patient post-endovascular aneurysm repair (EVAR). It also provides a computer program and associated hardware to implement the imaging method.

BACKGROUND OF THE INVENTION

An aneurysm is a localized dilation of a blood vessel and is characterized by a bulge in the wall of the blood vessel at the point of the aneurysm. Aneurysms may occur in any blood vessel. The natural evolution of an aneurysm is a diameter increase. And as an aneurysm increases in size, the risk of rupture increases. A ruptured aneurysm can lead to bleeding. A common example is an abdominal aortic aneurysm (AAA or "triple A"). A ruptured AAA typically leads to hypovolemic shock and, if left untreated, death.

Treatment of an aneurysm is often by way of an endovascular aneurysm repair (EVAR). EVAR is a type of endovascular surgery which involves the placement of an expandable stent graft within the vessel to treat the disease without operating directly on the vessel. A stent is a metal or plastic tube inserted into the lumen of the vessel. A wide variety of stents are available. EVAR is often preferable to open vessel surgery and is the most common technique for repair of AAA.

A life-long surveillance of the patient is required post-EVAR to ensure the integrity of the repair. The most common complication is an endoleak. An endoleak is a leak into the aneurysm sac after endovascular repair. Five types of endoleaks exist, of which type II is the most common. A type II endoleak is a retrograde flow to the aneurysm sac from branches, such as the lumbar and inferior mesenteric arteries into an aortic aneurysm. A type I endoleak is more serious, and results from the stent not sealing properly at the proximal or distal ends of the stent. This means that the aneurysm is still exposed to systolic blood pressure and can continue to grow. A type I typically requires re-intervention with a balloon catheter to seal the stent against the vessel walls. Less common but serious complications include type III and type IV endoleaks, which involve mechanical failure of the stent itself, which may result in surgical intervention.

Life-long surveillance after EVAR is troublesome for patients and physicians alike. In current clinical practice, the follow-up post-EVAR is performed using computed tomography (CT) imaging, most often involving an iodine contrast agent. The surveillance requires significant resources, and may be associated with harm owing to the risk of potentially unnecessary interventions, repeated exposure to radiation, and contrast nephrotoxicity from the contrast agent.

US 2015/0196250 discloses a co-registration system for detecting endoleaks associated with aneurysm repair. The system relies on a combination of captured functional parameters of the vessel, as well as data captured by intra- and extraluminal modalities. However, the focus is on intraluminal imaging, which relies on an invasive procedure for obtaining images.

U.S. Pat. No. 6,905,468 discloses an AAA evaluation and monitoring system. It uses a processor to determine aorta boundary information from converted scan information, and a calculation unit to calculate aorta diameter from boundary information. It contemplates storing images so that successive scans can be compared, but does not provide any detail of how the scans may be compared nor, particularly, how temporal evolution of the aneurysm can be assessed.

The article "Ultrasound fusion imaging with real-time navigation for the surveillance after endovascular aortic aneurysm repair" of Jin Hyon Joh at. al., Annals of Surgical Treatment and Research, vol. 92, no. 6, 1 Jan. 2017, pages 436-439, discloses coregistration of CT volume data with US data, using the origin of the left renal artery for coregistration.

SUMMARY OF THE INVENTION

There is therefore still a need for a convenient and less harmful approach to post-EVAR surveillance.

The invention is defined by the claims.

According to a first aspect of the invention, there is provided a method of patient monitoring following endovascular aneurysm repair with a bifurcated stent graft having a stent body and two stent legs defining a bifurcation point at the junction of the two legs, the method comprising the steps of:

receiving a previously generated first 3D volume scan of the stent in situ;

providing a second 3D volume scan of the stent in situ;

generating one or more fiducial markers in a first image derived from the first scan and in a second image derived from the second scan wherein one of the fiducial markers is the bifurcation point;

extracting a rigid 3D transform mapping based on the one or more fiducial markers;

applying a registration to the first and second scans based on the 3D rigid transform between the first and second images;

deriving a size value at the same location in the aneurysm from the first and second scans, where the same location is determined with reference to the registered first and second images of the stent; and comparing the size value from the first and second scans to assess a change in size of the aneurysm between the first and second scans.

The invention thus provides a post-EVAR monitoring method in which two scans taken at different times can be compared to assess aneurysm evolution. The scans are compared by identifying the same recognizable features in the stent in the two images, aligning the images based on the recognizable features and then applying a registration process based on the recognizable features. By applying a registration approach based on stent matching, the operator can avoid bias between different measurements in time, avoid an invasive procedure and apply the method to different imaging modes (e.g. CT, MRI and US). The first 3D volume scan may be performed shortly after the stent graft procedure and may have been performed by a different clinician to the second 3D volume scan which is when the change in size of the aneurysm is to be analyzed.

The size value is a parameter which is indicative of size. It may be a measure of length, area or volume.

The method is usually applied to an abdominal aortic aneurysm (AAA or "triple A"). EVAR is the most common treatment for AAA.

The location of the AAA also commonly occurs at or proximal to the aortic bifurcation (i.e. the point at which the abdominal aorta bifurcates into the left and right common iliac arteries). The result is the stent is also bifurcated, giving rise to a distinctive feature which can act as a fiducial marker. Thus, the stent is a bifurcated stent having a stent body and two stent legs defining a bifurcation point at the junction of the two legs, and one of the fiducial markers is the bifurcation point.

The first and second scans can be a 3D-computed tomography (CT) scan, a magnetic resonance imaging (MRI) scan and/or a 3D-ultrasound (US) scan. The registration step allows for multi-modality. In one embodiment, the first scan is a 3D-CT scan. This is typically the baseline scan obtained immediately or shortly after the EVAR procedure, e.g. within one month post-EVAR. In another embodiment, the second scan is a 3D-ultrasound scan. The first two scans are preferably where the first scan is a 3D-CT scan and the second scan is a 3D-US scan.

The method of the invention can be applied to any two scans. They may be consecutive (i.e. comparing the two most recent scans) or non-consecutive (for example always making a comparison with the first scan taken after the stent graft procedure), but the first and second scans are usually consecutive scans. The time between the first and second scans is from one month to the lifetime of the patient. By "lifetime of the patient" is meant the time between EVAR and death.

The registration applied to the first and second scans may be a user-guided registration. The method may also include a further step after the registration of applying an imaged-based refinement of the registration. Both of these steps can be used to improve any sub-optimal alignment of the images.

The size value is the diameter, area or volume of the aneurysm (i.e. the residual sac). Any of these values can be quantified and can give a measure of disease progression. In a further embodiment, the method further comprises the step of using the change in size to make a clinical evaluation of disease progression.

In another aspect, the invention provides a computer program comprising a computer program code which is adapted, when the program is run on a computer, to implement the present method.

In a further aspect, the invention provides a controller for imaging a stent following endovascular aneurysm repair with bifurcated stent graft having a stent body and two stent legs defining a bifurcation point at the junction of the two legs, wherein the controller is adapted to:

receive a previously generated first 3D volume scan of the stent in situ;

acquire a second 3D volume scan of the stent in situ;

generate one or more fiducial markers in a first image derived from the first scan and in a second image derived from the second scan, wherein one of the fiducial markers is the bifurcation point;

extract a rigid 3D transform mapping based on the one or more fiducial markers;

apply a registration to the first and second scans based on the 3D rigid transform between the first and second images;

derive a size value at the same location in the aneurysm from the first and second scans, where the same location is determined with reference to the registered first and second images of the stent; and compare the size value from the first and second scans to assess a change in size of the aneurysm between the first and second scans.

In a still further aspect, the invention provides an imaging system comprising the above-mentioned controller, a transducer, a beamformer and a display device.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a method of patient monitoring following EVAR using 3D-imaging to show any changes in size of the stent over time.

The invention provides a method of patient monitoring following endovascular aneurysm repair (EVAR) with a stent graft. It particularly applies to abdominal aortic aneurysm repair.

A first 3D volume scan of the stent in situ is provided and a second, subsequent 3D volume scan of the stent is also provided. One or more fiducial markers are generated in a first image derived from the first scan and in a second image derived from the second scan. The fiducial markers identify recognizable features of the stent, such as the bifurcation point in the stent graft. A rigid 3D transform mapping based on the one or more fiducial markers is extracted and then a registration is applied to the first and second scans based on the 3D rigid transform between the first and second images. A size value is derived at the same location in the aneurysm from the first and second scans. The same location is determined with reference to the registered first and second images of the stent. A comparison of the size value from the first and second scans is used to assess a change in size of the aneurysm between the first and second scans. This change in size allows the clinician to evaluate disease progression.

In a preferred embodiment, at least two fiducial markers are generated, and more preferably at least three fiducial markers are generated (e.g. 3-6). Most commonly three fiducial markers are generated.

A post-EVAR patient will typically present having already had a 3D volume scan of their stent in situ. This scan is usually performed immediately or shortly after the procedure. The 3D volume scan is usually performed by CT imaging. CT imaging post-EVAR is a widely used and well-established technique and further discussion is therefore not required.

The scan obtained immediately or shortly after the procedure forms a baseline scan and provides a measure of the stent and aneurysm shortly after the procedure. It is typically obtained within one month of the EVAR procedure (i.e. post-EVAR).

Subsequent scans are preferably provided by ultrasound, as this technique does not require the injection of a contrast agent. The two scans are compared to monitor disease progression based on changes in the size of the stent.

The invention relies on a conventional ultrasound transducer. As is known in the art, a conventional ultrasound transducer, in use, transmits and receives an ultrasound beam. It is positioned externally at the site of interest on the patient, e.g. over the abdominal aorta.

Figure 1:
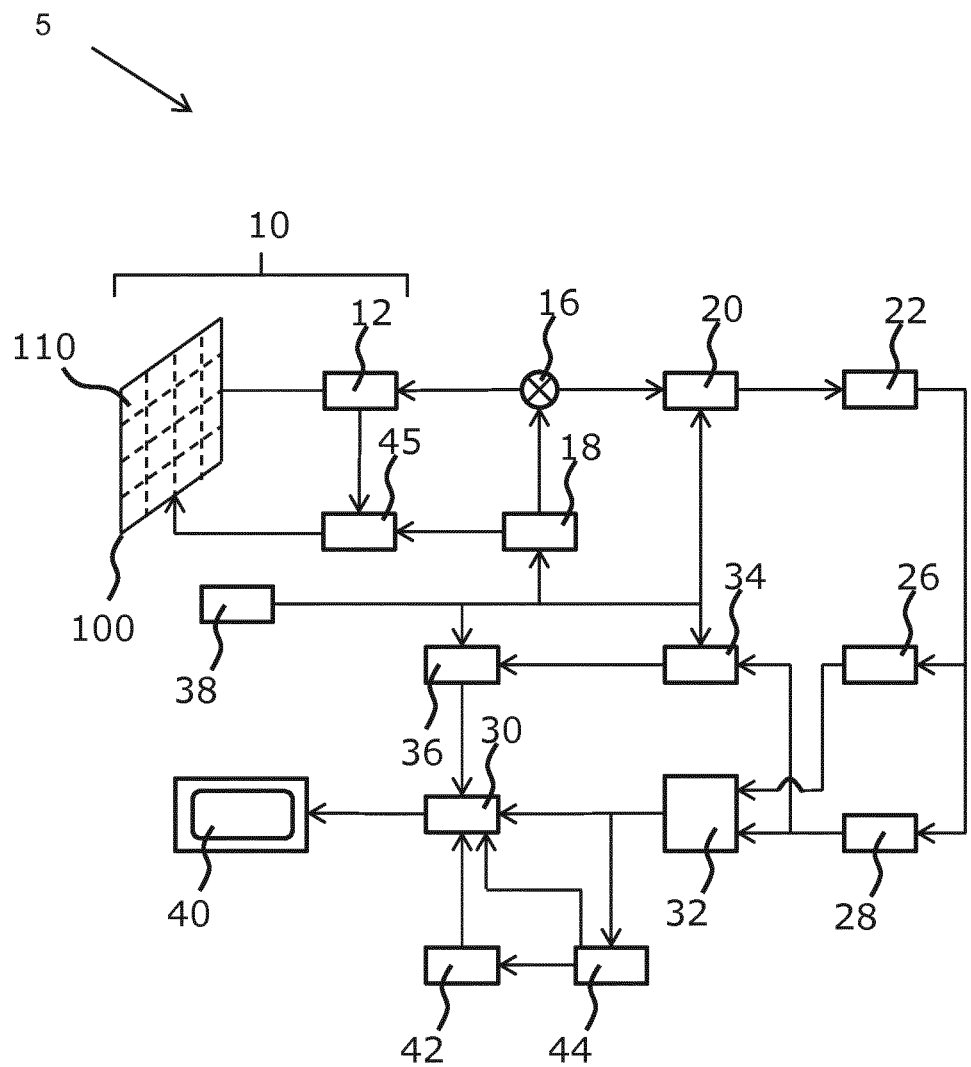
FIG. 1 shows a general operation of an exemplary ultrasound diagnostic imaging system.

The general operation of an exemplary ultrasound diagnostic imaging system will first be described, with reference to FIG. 1.

The system comprises an array transducer probe 10 which has a capacitive micromachined ultrasonic transducer (CMUT) array 100 for transmitting ultrasound waves and receiving echo information. The CMUT transducer array 100 may alternatively comprise piezoelectric transducers formed of materials such as PZT or PVDF. The CMUT transducer array 100 is a two-dimensional array of transducers 110 capable of scanning in a 2D plane or in three dimensions for 3D imaging. In another example, the CMUT transducer array 100 may be a 1D array, although such an approach requires additional spatial position tracking, such as electromagnetic (EM) or optical tracking.

The CMUT transducer array 100 is coupled to a microbeamformer 12 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 12 is coupled by the probe cable to a transmit/receive (T/R) switch 16 which switches between transmission and reception and protects the receive main beamformer 20 from high energy transmit signals when a microbeamformer is not used and the CMUT transducer array 100 is operated directly by the main system beamformer. The transmission of ultrasound beams from the CMUT transducer array 100 is directed by a transducer controller 18 coupled to the microbeamformer by the T/R switch 16 and a main transmission beamformer (not shown), which receives input from the user's operation of the user interface or user control panel 38.

One of the functions controlled by the transducer controller 18 is the direction in which beams are steered and focused. Beams may be steered straight ahead from (orthogonal to) the CMUT transducer array 100, or at different angles for a wider field of view. The transducer controller 18 can be coupled to control a DC bias control 45 for the CMUT array. The DC bias control 45 sets DC bias voltage(s) that are applied to the CMUT cells.

In the reception channel, partially beamformed signals are produced by the microbeamformer 12 and are coupled to a receive main beamformer 20 where the partially beamformed signals from individual patches of transducers are combined into a fully beamformed signal. For example, the receive main beamformer 20 may have 128 channels, each of which receives a partially beamformed signal from a patch of dozens or hundreds of CMUT transducer cells or piezoelectric elements. In this way the signals received by thousands of transducers of a CMUT transducer array 100 can contribute efficiently to a single beamformed signal.

The beamformed reception signals are coupled to a signal processor 22. The signal processor 22 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and microbubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed to take into account the characteristics of the transmission beamformer. In FIG. 1 only the microbeamformer 112 and the receive main beamformer 20 are shown, for simplicity. In the complete system, there will also be a transmission chain with a transmission micro beamformer, and a main transmission beamformer.

The function of the microbeamformer 12 is to provide an initial combination of signals in order to decrease the number of analog signal paths. This is typically performed in the analog domain.

The final beamforming is done in the receive main beamformer 20 and is typically after digitization.

The transmission and reception channels use the same CMUT transducer array 100 which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 26 and a Doppler processor 28. The B mode processor 26 employs detection of an amplitude of the received ultrasound signal for the imaging of structures in the body such as the tissue of organs, vessels in the body or in the case of the invention, stents. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor 28 typically includes a wall filter with parameters which may be set to pass and/or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on a display device 40. In addition to being used for imaging, the blood flow values produced by the Doppler processor 28 and tissue structure information produced by the B mode processor 26 are coupled to a quantification processor 34. The quantification processor 34 produces measures of different flow conditions such as the volume rate of blood flow as well as structural measurements such as the sizes of organs and gestational age. The quantification processor 34 may receive input from the user control panel 38, such as the point in the anatomy of an image where a measurement is to be made. Output data from the quantification processor 34 is coupled to a graphics processor 36 for the reproduction of measurement graphics and values with the image on the display device 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user control panel 38, such as patient name. The user control panel 38 is also coupled to the transmit transducer controller 18 to control the generation of ultrasound signals from the CMUT transducer array 100 and hence the images produced by the CMUT transducer array 100 and the ultrasound system. The transmit control function of the transducer controller 18 is only one of the functions performed. The transducer controller 18 also takes account of the mode of operation (given by the user) and the corresponding required transmitter configuration and band-pass configuration in the receiver analog to digital converter. The transducer controller 18 can be a state machine with fixed states.

The user control panel 38 is also coupled to the multi-planar reformatter 44 for selection and control of the planes of multiple multi-planar reformatted (MPR) images which may be used to perform quantified measures in the image field of the MPR images. transducer controller 18, the quantification processor 34 and the graphics processor 36. Alternatively, the processor arrangement may be an additional module.

Effective acoustic contact is required between the array transducer probe 10 and the body of the patient being scanned in order to create high-quality ultrasound images. Effective acoustic contact is facilitated by the application of coupling gel to the array transducer probe 10 and skin of the patient and by the sonographer maintaining good acoustic coupling by forcefully pressing the array transducer probe 10 against the skin of the patient.

It should be noted that this is not the case with CT imaging, where the radiation beams pass through the air and readily penetrate the body without physical contact of an instrument.

The method of the invention will now be described with reference to FIGS. 2-6. In an embodiment of the invention, the method may be implemented by a computer program code, included in a computer program product, which is run on a computer.

Figure 2:
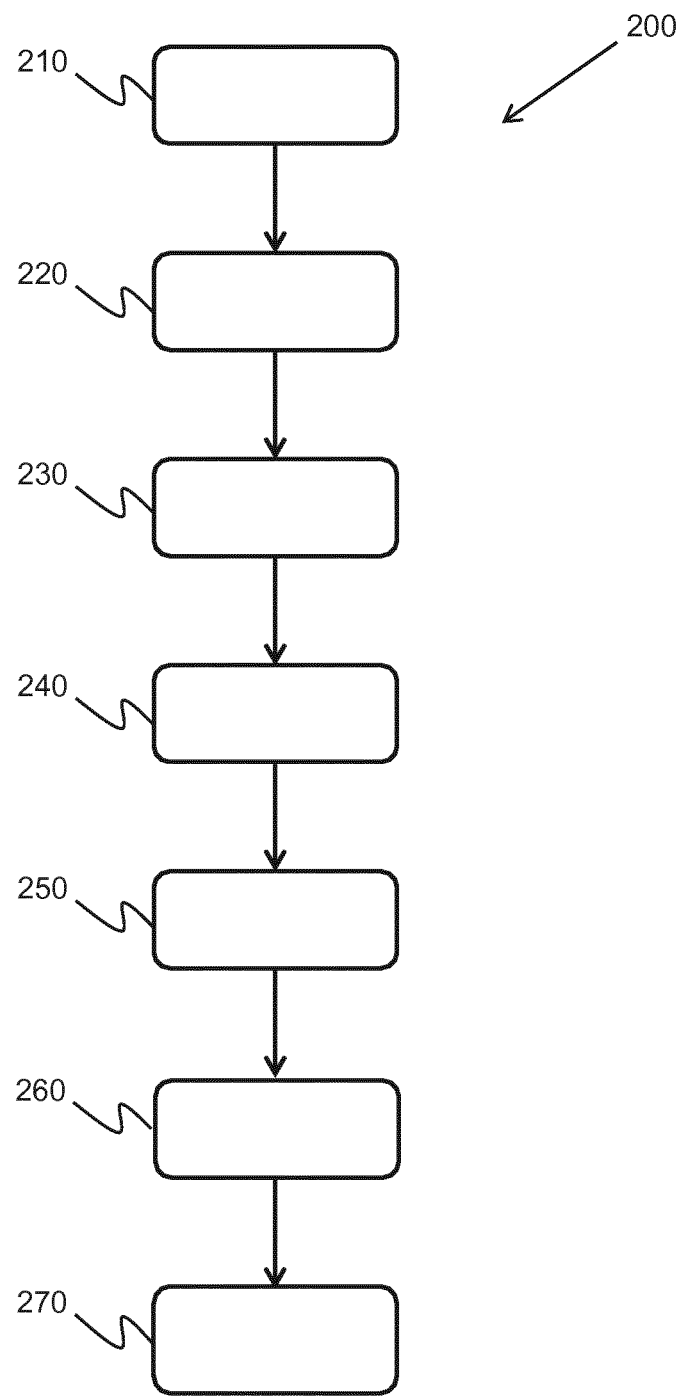
FIG. 2 shows a flowchart of the method for patient monitoring according to the invention.

FIG. 2 shows a flowchart of the method 200 for patient monitoring following EVAR. The method 200 commences in step 210.

In step 210, a first 3D volume scan of the stent in situ is provided. By "in situ" is meant that the stent graft has been grafted (which typically involves placing the stent via a catheter inserted in the femoral artery) in the required position in the patient's body at the site of the aneurysm. The first 3D volume scan may be the baseline scan obtained immediately or shortly after the EVAR procedure. In this embodiment, the 3D volume scan is likely to be a 3D-CT volume scan. Alternatively, the first 3D volume scan may be a subsequent scan which has been taken from the patient. This could either be another 3D-CT volume scan, or it could be a 3D-US volume scan.

At the time the method of the invention is performed, this scan would already have been acquired and the invention relies on the scan having been saved.

In step 220, a second 3D volume scan of the stent in situ is provided. The second scan must be obtained after the first scan so that the temporal evolution of the aneurysm can be determined. The second 3D volume scan is preferably obtained by 3D-US. The method may be applied at the same time the second scan is acquired, although saved after acquisition of the scan and the method applied later. In a preferred embodiment, the invention includes the step of acquiring the second 3D volume scan of the stent in situ.

The second scan may be obtained by the US method described with reference to FIG. 1.

In step 230, one or more fiducial markers are generated in the first and second images. The fiducial markers identify recognizable features of the stent, such as the bifurcation point in a bifurcated stent. Of course, the fiducial markers need to be common to both images. An example is shown in FIG. 3.

Figure 3:
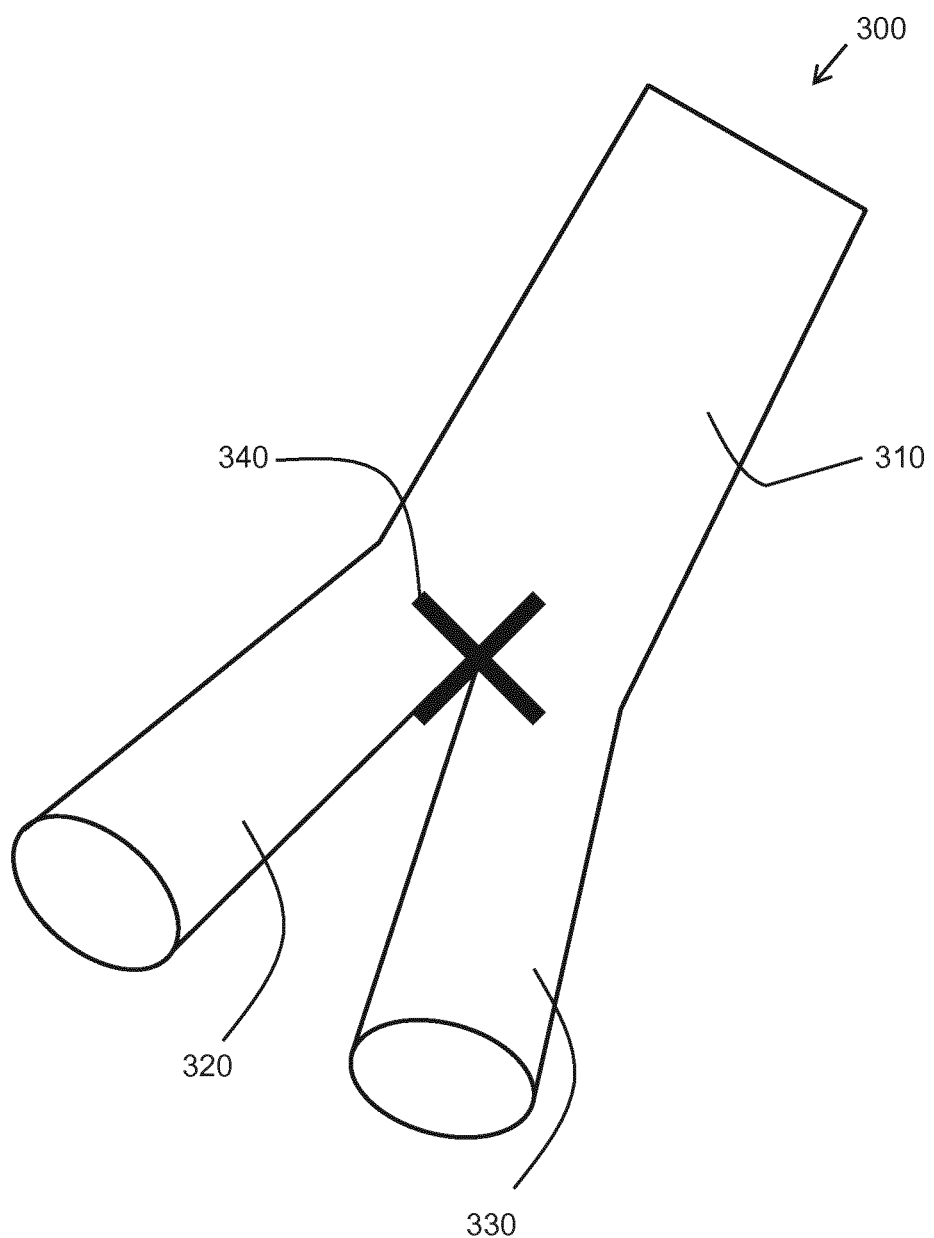
FIG. 3 is a representation of a bifurcated stent of the type used in EVAR treatment of AAA.

FIG. 3 shows a representation of a bifurcated stent 300 of the type used in EVAR treatment of AAA. The stent graft is a bifurcated stent graft having a stent body 310 and two stent legs 320,330 defining a bifurcation point 340 at the junction of the two legs, and wherein one fiducial marker (marked with an X) is the bifurcation point 340 which is a distinctive feature of the AAA stent graft post-EVAR. The position is selected as the most proximal for stent legs, located within distal part of main body.

The shape of the stent graft corresponds to the anatomy of the abdominal aorta since the aneurysm commonly occurs at or proximal to the aortic bifurcation (i.e. the point at which the abdominal aorta bifurcates into the left and right common iliac arteries). The result is the stent is also bifurcated, giving rise to a distinctive feature which can act as one of the fiducial markers.

In order to detect the bifurcation, transducer controller 18 is used to detect tubular shapes at two different scales. A larger scale is used to detect the main body of the stent, and a smaller scale detector is used to detect the stent legs. The stent legs bifurcation position (340, marked with an X in FIG. 3) is then estimated. The tubular shapes of the stent legs and main body are for example found by parsing 2D transverse slices from the 3D scan data and performing shape recognition, such as circle detection.

Returning to FIG. 2, in step 240, a rigid 3D transform mapping based on the one or more fiducial markers is extracted. Using the smaller scale detection, the orientation of the stent legs can be estimated for the first and second scans. If the legs orientations are not parallel, then the subsequent registration is directly feasible, since the legs uniquely define the rigid body transform between the two volumes. However, if the legs orientations are parallel, there remains an unknown in the registration transform, related to the longitudinal position of the stent in both volumes. In such cases, a user-based assessment of the registration is necessary. In case of remaining translation, the user could click in both volumes to provide the fiducial position, thus removing the uncertainty of registration.

A rigid 3D transform mapping includes rotations, translations or their combination. Reflections are also sometimes included in the definition of rigid 3D transforms, but are not needed in this situation. Essentially, a transform mapping defines the mapping between the stent image in one image scan and in the other image scene, and hence defines the mapping between those images as a whole. The smaller class of transformations is known as proper rigid transformations. Any object will keep the same shape and size after a proper rigid transformation. The effect of the registration is to align the imaged volumes.

Figure 4:
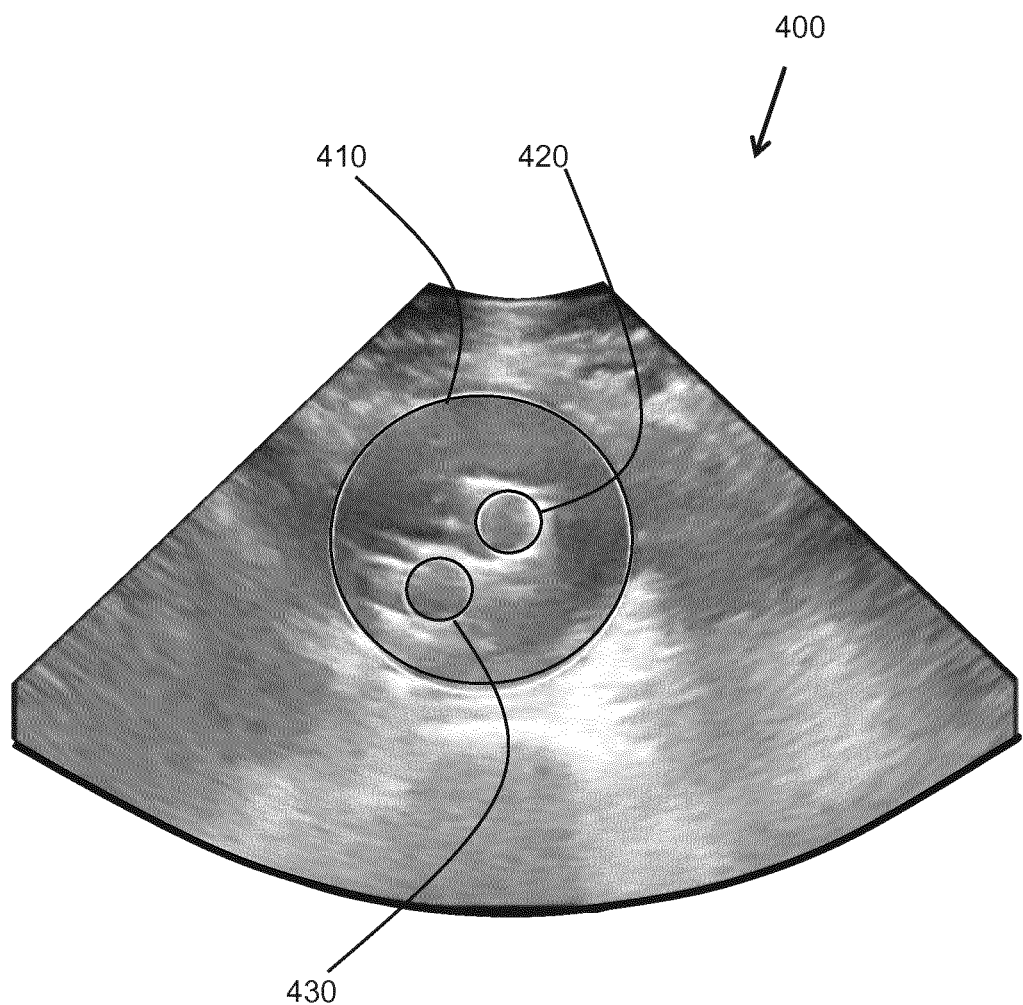
FIG. 4 is an ultrasound image showing the circular shape detector run at two different scales in order to extract stent main body and legs.

FIG. 4 is an ultrasound image 400 showing the circular shape detector run at two different scales in order to extract aneurysm sac 410 and legs 420,430.

As mentioned above, the stent legs and main body are for example found by parsing 2D transverse slices from the 3D scan data and performing shape recognition, such as circle detection. The fiducial point is automatically identified to trigger the registration.

Figure 5:
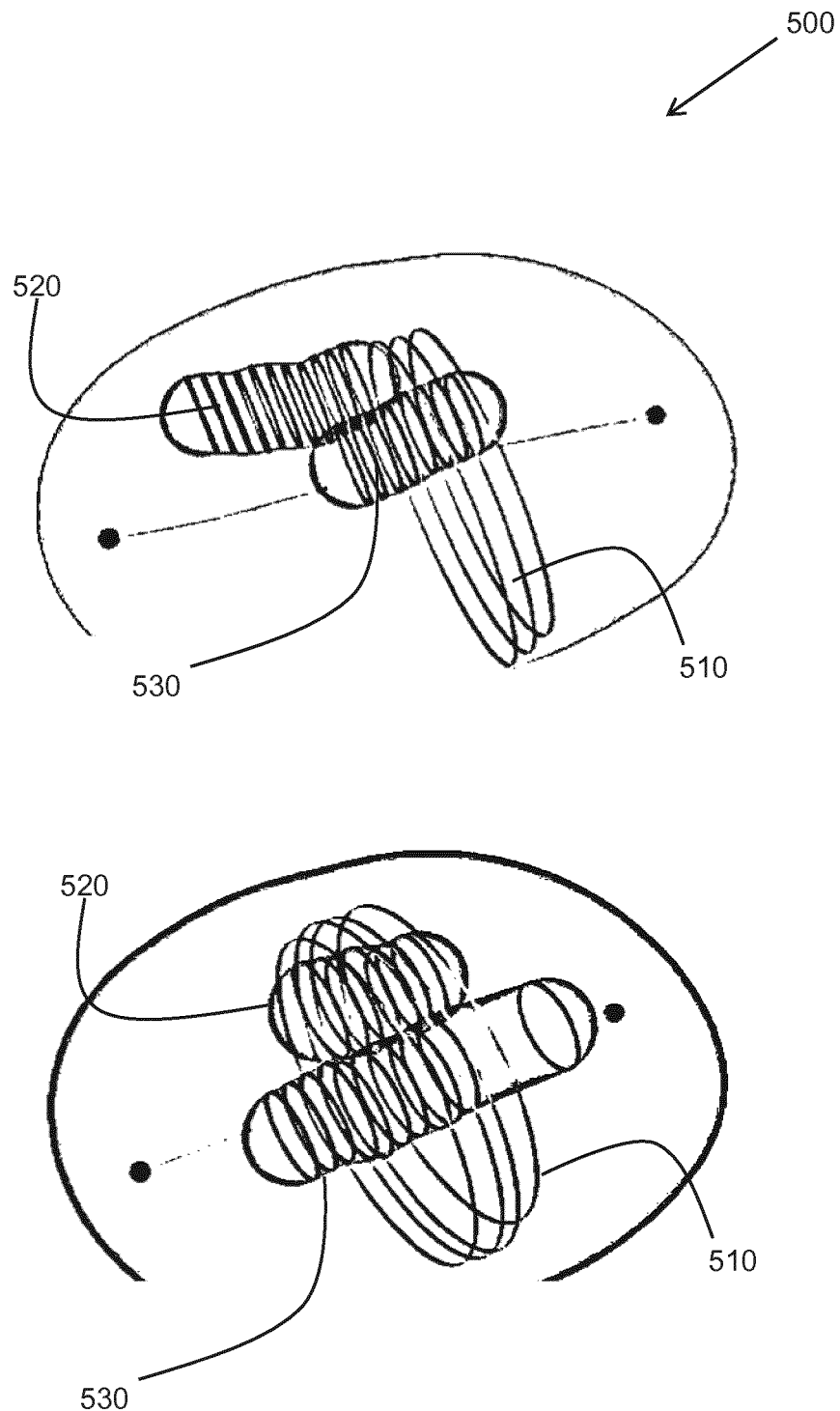
FIG. 5 shows the results of a baseline scan and for the same stent at 1 year follow-up.

FIG. 5 shows the results of a first and second scan of the main body 510 and legs 520,530 and for a stent at baseline (top) obtained by CT and for the same stent at 1 year follow-up (bottom).

FIG. 5 also shows the center line of the vascular balloon 540. The center line can be used as a main axis orientation. A point in the legs 520,530 may be used as another fiducial marker.

Returning again to FIG. 2, in step 250, a registration is applied to the first and second scans based on the 3D rigid transform between the first and second images. Image registration is a known process of transforming one or more images into a coordinate system of a reference image. The registration method will be briefly discussed with reference to FIG. 6.

Figure 6:
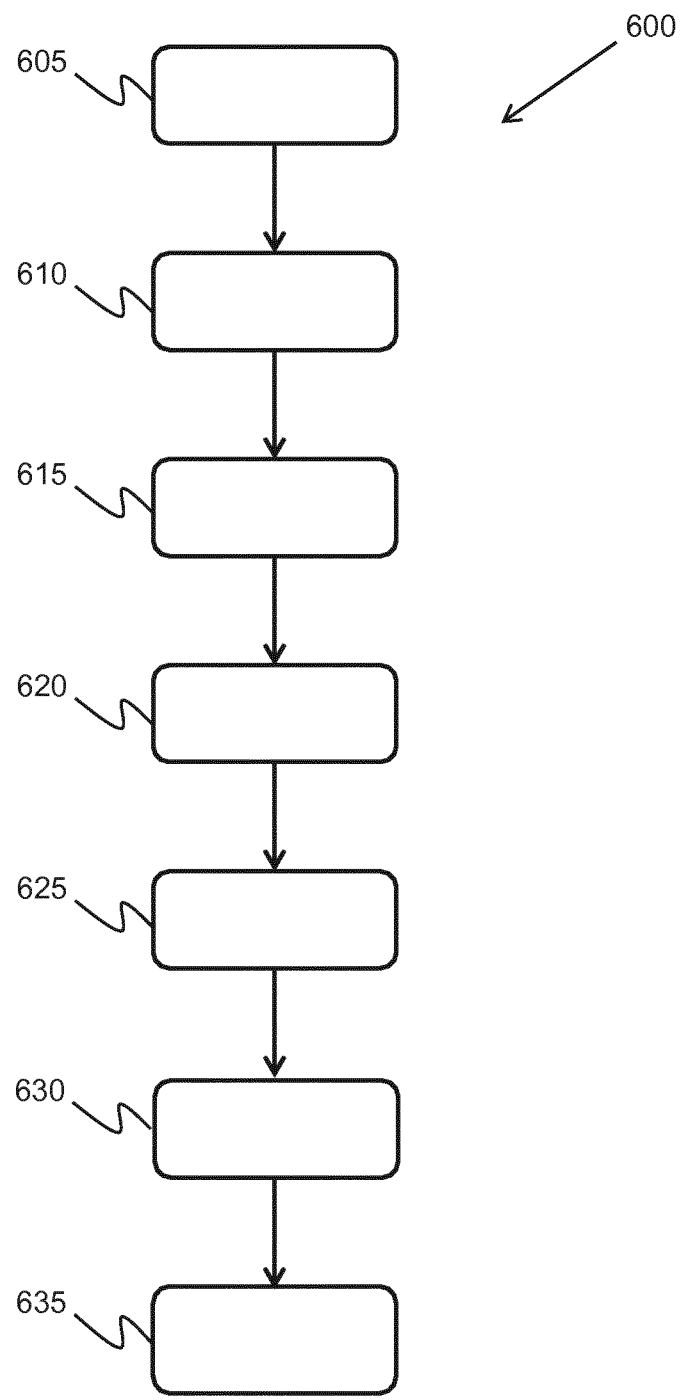
FIG. 6 is a flowchart of the registration method of the invention.

FIG. 6 is a flowchart of the registration method 600 of the invention.

In operation 605, a 3D-CT, 3D-MRI or 3D-US dataset is obtained from a first 3D volume scan of the stent in the patient.

In operation 610, one or more fiducial markers, e.g. the stent graft bifurcation point, the center line and a position on the legs, are marked or identified in the 3D-CT/MRI/US image dataset. As explained above, they may be found based on identification of the different portions of the stent by analysis of 2D image slices. Preferably, two or more fiducial markers are used, so that position alignment and orientation alignment are enabled. One of these fiducial markers is the bifurcation point.

In operation 615, the fiducial markers generated from the 3D-CT/MRI/US image generated in operation 605 are saved with the associated imaging data.

In operation 620, the image dataset is stored in a memory. The data may be transferred via wireless link, via a network (e.g. an intranet or internet), via a portable data storage medium such as a DVD or a Flash memory device, etc. In some embodiments, the image dataset may be transferred from the imaging apparatus to a network server and associated data storage device, and then transferred from the network server to an US apparatus.

In operation 625, a second 3D volume scan of the stent is performed on the region of interest (here, the stent). The imaging may be performed by imaging system 5 of FIG. 1.

In operation 630, the same fiducial markers are generated from the second 3D volume scan generated in operation 625. This may be fully automated, but there is also the option of providing feedback to a user of the system and receiving user input of the fiducial positions (where the image quality is not good enough for fully automatic identification of fiducial markers in the images).

The fiducial markers for the second 3D volume scan are employed in registering the second 3D volume scan with the dataset obtained from the first 3D volume scan in operation 605. Where user (clinician) input is enabled, the clinician may employ a user interface (e.g. a mouse, trackball, touch screen, lighten, etc.) and a software algorithm executed by a processor (e.g. image processor 30) to add the fiducial markers to the scan.

In operation 635, the second 3D volume scan produced in operation 625 is registered (or fused) with the stored 3D-CT/MRI/US image dataset obtained in operations 605-615 by means of the fiducial markers generated in operations 615 and 630. By employing the fiducial markers, the image registration may be limited to dataset translation and rotation, both linear transformations. The required linear registration procedure for example is based on detecting the main direction of alignment of the stent graft as well as the detection of the leg orientations. In this way, the two 3D scans may be made to overlap by using a suitable 3D alignment operation.

This registration may also be fully automated, but there is also the option of providing feedback to a user of the system and receiving user input for example of the stent orientation to assist in the registration procedure.

The implementation of such image registration algorithms would be within the capabilities of those skilled in the art, and further details of such algorithms are not repeated here.

Two well-known transformation models are rigid and non-rigid transformations. Rigid transformations are linear transformations, which include translation and rotation transforms. In contrast, non-rigid transformations also locally warp an image to align the image with the reference image. The registration used in the invention is a rigid registration since this is suited to a rigid object which does not change in size over time, like a stent.

An imaged-based refinement of the registration may optionally be applied at this point. This involves refinement based on a metric other than the fiducial markers, such as intensities. This may be applied where the alignment after registration is sub-optimal but close to a solution. Differences in the registration can be minimized using small image-guided adjustments.

The registration process provides a volume-to-volume alignment between the first and second 3D volume scans.

Disease progression can also be observed over time by comparing multiple pairs of scans, which may either be consecutive or non-consecutive. The registration step does not exclude one or more further images being included based on the same fiducial markers, although preferably only two-at-a-time are compared.

Returning to FIG. 2, in operation 260, a size value is derived at the same location in the aneurysm from the first and second scans. Looking at the same location is the appropriate way to assess any change in size over time. The same location in the aneurysm is determined with reference to the registered first and second images of the stent. This is a significant improvement over a visual inspection of the scans since a visual inspection does not ensure that the user is looking at precisely the same locations. The size value may be the stent diameter, area or volume (units will typically be cm, $cm^2$ or $cm^3$, respectively). The change is typically quantified and provided on the display device 40.

By comparing the size values from the first and second scans in a operation 270, one can assess a change in size of the aneurysm between the first and second scans. The change in size can be used to make a clinical evaluation of disease progression. If it indicates a sac growth, then endoleak is suspected. If the volume decreases, then the probability of endoleak is lower and the rupture risk is very low.

The patient will have many follow up scans in his/her lifetime post-EVAR. The invention can be applied in comparing any two scans. Accordingly, the time between the first and second scans may be anything from one month to the lifetime of the patient. However, more usually, the first and second scans are consecutive scans. Accordingly, the time between the first and second scans is preferably 6-24 months. A common timescale between consecutive scans is about a year.

In one embodiment, the first scan is the baseline scan, which is the first scan obtained after the procedure. That is, immediately or shortly after the procedure. In practice, this tends to be within one month post-EVAR. The first scan is usually a 3D-computed tomography scan, although it could be a 3D-ultrasound scan. The second scan is preferably a 3D-ultrasound scan since this can be performed without a contrast agent.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A method of patient monitoring following endovascular aneurysm repair with a bifurcated stent graft having a stent body and two stent legs defining a bifurcation point at a junction of the two stent legs, the method comprising:
    receiving a previously generated first 3D volume scan of the bifurcated stent graft in situ;
    providing a second 3D volume scan of the bifurcated stent graft in situ;
    generating one or more fiducial markers in a first image derived from the first scan and in a second image derived from the second scan, wherein one of the fiducial markers is the bifurcation point;
    extracting a rigid 3D transform mapping based on the one or more fiducial markers;
    applying a registration to the first and second scans based on the 3D rigid transform between the first and second images;
    deriving a size value at the same location in the aneurysm from the first and second scans, where the same location is determined with reference to the registered first and second images of the bifurcated stent graft; and
    comparing the size value from the first and second scans to assess a change in size of the aneurysm between the first and second scans.

2. The method as claimed in claim 1, wherein the aneurysm is an abdominal aortic aneurysm.

3. The method as claimed in claim 1, wherein the first scan is a 3D-computed tomography scan.

4. The method as claimed in claim 1, wherein the second scan is a 3D-ultrasound scan.

5. The method as claimed in claim 1, wherein the first scan is a baseline scan obtained within one month post-endovascular aneurysm repair.

6. The method as claimed in claim 1, wherein a time between the first and second scans is from one month to a lifetime of the patient.

7. The method as claimed in claim 1, wherein the first and second scans are consecutive scans.

8. The method as claimed in claim 1, wherein the registration applied to the first and second scans is a user-guided registration.

9. The method as claimed in claim 1, wherein the method includes a further step after the registration of applying an imaged-based refinement of the registration.

10. The method as claimed in claim 1, wherein the size value is a diameter, area or volume of the aneurysm.

11. The method as claimed in claim 1, further comprising step of using the change in size to make a clinical evaluation of disease progression.

12. A tangible, non-transitory computer readable medium, which stores instructions, wherein the instructions, when executed by a processor, cause the processor to perform the method of claim 1.

13. A controller for imaging a stent following endovascular aneurysm repair with a bifurcated stent graft having a stent body and two stent legs defining a bifurcation point at a junction of the two stent legs, wherein the controller is adapted to:
    receive a previously generated first 3D volume scan of the bifurcated stent graft in situ;
    acquire a second 3D volume scan of the bifurcated stent graft in situ;
    generate one or more fiducial markers in a first image derived from the first scan and in a second image derived from the second scan, wherein one of the fiducial markers is the bifurcation point;
    extract a rigid 3D transform mapping based on the one or more fiducial markers;
    apply a registration to the first and second scans based on the 3D rigid transform between the first and second images;
    derive a size value at the same location in the aneurysm from the first and second scans, where the same location is determined with reference to the registered first and second images of the bifurcated stent graft; and
    compare the size value from the first and second scans to assess a change in size of the aneurysm between the first and second scans.

14. The controller of claim 13, wherein the aneurysm is an abdominal aortic aneurysm.

15. The controller as claimed in claim 13, wherein the first scan is a 3D-computed tomography scan.

16. The controller as claimed in claim 13, wherein the second scan is a 3D-ultrasound scan.

17. The controller as claimed in claim 13, wherein the first scan is a baseline scan obtained within one month post-endovascular aneurysm repair.

18. An imaging system, comprising:
a beamformer;
a display device;
a controller; and
a tangible, non-transitory computer readable medium, which stores instructions, which when executed by the controller, cause the controller to: receive a previously generated first 3D volume scan of a stent in situ; acquire a second 3D volume scan of the stent in situ; generate one or more fiducial markers in a first image derived from the first scan and in a second image derived from the second scan, wherein one of the fiducial markers is a bifurcation point; extract a rigid 3D transform mapping based on the one or more fiducial markers; apply a registration to the first and second scans based on the 3D rigid transform between the first and second images; derive a size value at the same location in an aneurysm from the first and second scans, where the same location is determined with reference to the registered first and second images of the stent; and compare the size value from the first and second scans to assess a change in size of the aneurysm between the first and second scans.

19. The controller of claim 18, wherein the aneurysm is an abdominal aortic aneurysm.

20. The imaging system as claimed in claim 18, wherein the first scan is a 3D-computed tomography scan.

21. The imaging system as claimed in claim 18, wherein the second scan is a 3D-ultrasound scan.

22. The imaging system as claimed in claim 18, wherein the first scan is a baseline scan obtained within one month post-endovascular aneurysm repair.

\* \* \* \* \*